United States Patent [19]

Jung et al.

[11] Patent Number: 5,391,794
[45] Date of Patent: Feb. 21, 1995

[54] THREE-LEGGED SILANE COUPLING AGENTS AND THEIR PREPARATION METHODS

[75] Inventors: Il N. Jung; Gyu H. Lee; Mi Y. Suk, all of Seoul; Seung H. Yeon, Kyungki-Do, all of Rep. of Korea

[73] Assignee: Korea Institute of Science and Technology, Seoul, Rep. of Korea

[21] Appl. No.: 187,054

[22] Filed: Jan. 27, 1994

[51] Int. Cl.$^6$ ............................ C07F 7/08; C07F 7/10
[52] U.S. Cl. .................................. 556/435; 556/415; 549/215
[58] Field of Search .................. 556/435, 415; 549/215

[56] References Cited

U.S. PATENT DOCUMENTS

| | | | |
|---|---|---|---|
| 5,026,893 | 6/1991 | Paciorek et al. | 556/435 |
| 5,233,069 | 8/1993 | Jung et al. | 556/435 |
| 5,235,083 | 8/1993 | Jung et al. | 556/435 |
| 7,788,312 | 11/1988 | Paciorek et al. | 556/435 |

*Primary Examiner*—Paul F. Shaver
*Attorney, Agent, or Firm*—Oblon, Spivak, McClelland, Maier & Neustadt

[57] ABSTRACT

The present invention relates to trissilylalkanes represented by formula (X), (XI), (XII), (XIII), (XIV), (XV), (XVI) and (XVII), and preparation methods thereof.

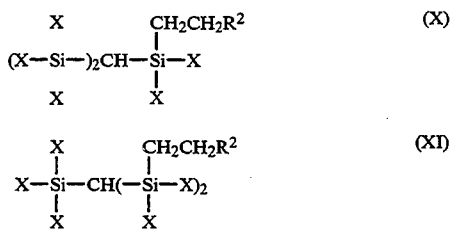

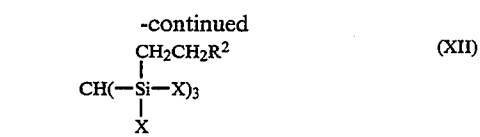

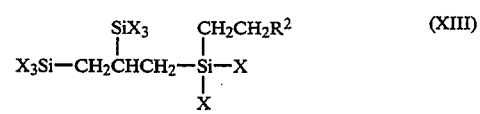

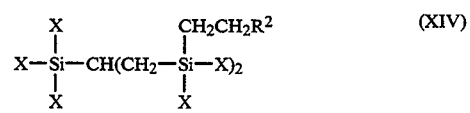

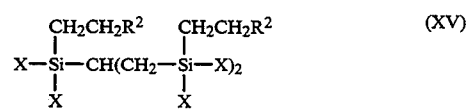

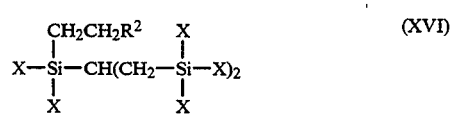

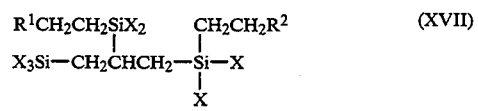

wherein X can be Cl, $OR^1$ ($R^1=C_1-C_4$ alkyl) or OAc, and $R^2$ can be Ph, $CH_2Cl$, $C_nH_{2n}CH_3$ (n=0-15), $Si(Me)_mCl_{3-m}$, (m=0-3), $CF_3$, CN, $CH_2CN$, $CH=CH_2$, $(CH_2)_4CH=CH_2$,

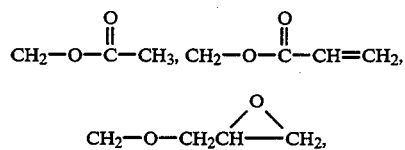

Ph-$CH_2Cl$ or cyclohex-3-enyl group.

17 Claims, No Drawings

THREE-LEGGED SILANE COUPLING AGENTS AND THEIR PREPARATION METHODS

BACKGROUND OF THE INVENTION

1. Field of the Invention

This present invention relates to new trissilylalkane organosilicon compounds with a various organic group substituents which can be used as coupling agents between organic material and inorganic filler in plastic industry and their preparation method. As is well known in the art, plastics generally comprise a polymeric material, a filler or pigment and a coupling agent that is capable of forming a connection or bond between the filler and rubber polymer. Thus, the coupling agent serves as a crosslinker that is chemically or physically bonded to both the filler and polymer. This invention relates to new three legged silane coupling agents represented by the Formulas (X), (XI), (XII), (XIII), (XIV), (XV), (XVI) and (XVII), and their preparation methods by reacting trissilylalkanes represented by the Formulas (I), (II), (III), (IV), (V), (VI), (VII) and (VIII) with cyclohexene or unsaturated organic compounds represented by the Formula (IX) in the presence of hydrosilation catalysts such as chloroplatinic acid, platinum on silica, tributyl amine, and inorganic complexes of Pd, Rh, Ni, etc.

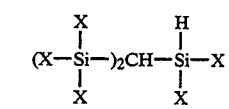 (I)

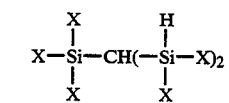 (II)

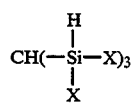 (III)

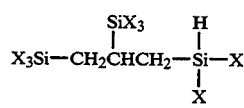 (IV)

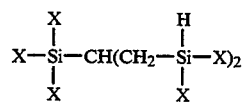 (V)

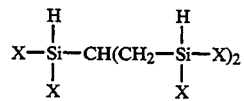 (VI)

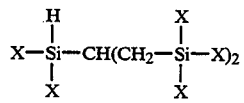 (VII)

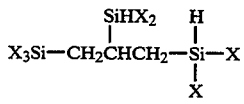 (VIII)

wherein X represents Cl, $OR^1$ ($R^1$ is alkyl ($C_1$-$C_4$)) or OAc in Formula (I), (II), (III), (IV), (V), (VI), (VII), and (VIII).

$$CH_2=CH-R^2 \quad (IX)$$

wherein $R^2$ can be Ph, $CH_2Cl$, $C_nH_{2n}CH_3$ (n=0-15), $Si(Me)_mCl_{3-m}$ (m=0-3), $CF_3$, CN,

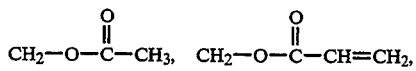

$CH=CH_2$, $(CH_2)_4CH=CH_2$,

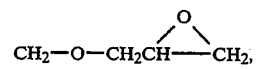

Ph-$CH_2Cl$, $CH_2CN$ or cyclohex-3-enyl group.

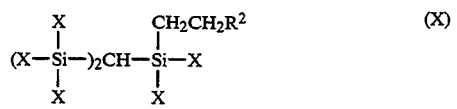 (X)

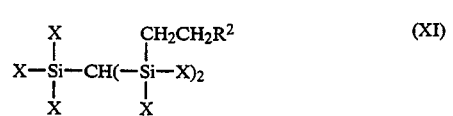 (XI)

 (XII)

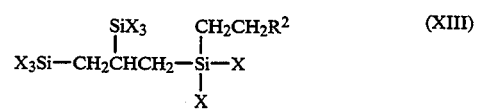 (XIII)

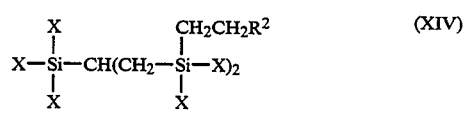 (XIV)

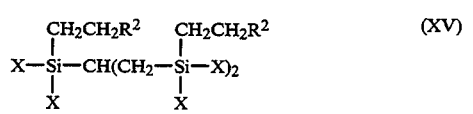 (XV)

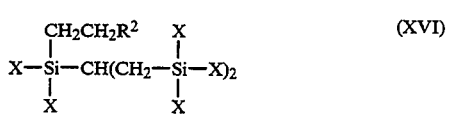 (XVI)

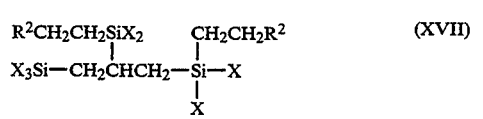 (XVII)

wherein X can be Cl, $OR^1$ ($R^1$ is alkyl ($C_1$-$C_4$)) or OAc, and $R^2$ can be Ph, $CH_2Cl$, $C_2CH_{2n}CH_3$ (n=0-15), $Si(Me)_mCl_3$ (m=0-3), $CF_3$, CN, $CH_2CN$, $CH=CH_2$, $(CH_2)_4CH=CH_2$,

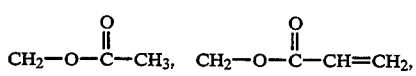

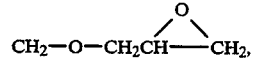

Ph-CH₂Cl or cyclohex-3-enyl group.

2. Descriptions of the Prior Art

Applications of coupling agents for surface modification of fillers and reinforcements in plastics have generally been directed toward improved mechanical strength and chemical resistance of composites related to improved adhesion crossed the interface. Silane coupling agents, used in a wide range of composite products, enable the plastic compounder to maximize, as economically as possible, the contributions of individual components to the properties of the composites. All commercial silane coupling agents are represented by the general formula (RO)₃Si—A—Y. The trialkoxysilyl group, —Si (OR)₃ of the coupling agents hydrolyze stepwise in water to give the corresponding silanols, —Si(OH)₃, which ultimately condense with the hydroxy groups on the surface of mineral surfaces to provide a bond to the inorganic components. This bonding maintains good adhesion to the most siliceous or metal oxide fillers and reinforcements. The organofunctional groups, Y are chosen for reactivity or compatibility with the polymer. The organic group, A is a chemical linkage between the organofunctional group and silicon. γ-Chloropropyltrimethoxysilane is one of the most widely used coupling agents.

Most of standard methods for forming Si—C bonds may be used in preparing intermediates for silane coupling agent synthesis. In the preparation of silane coupling agents, trichlorosilane with carbon-carbon unsaturated compounds through hydrosilation and introduce various organic groups Since the chlorine groups on silicon are easily hydrolyze and give highly toxic hydrogen chawride, chlorosilanes are reacted with alcohol and converted to alkoxysilanes. This hydrosilation can occur, but proceeds better in the presence of noble metal catalysts such as platinum, chloroplatinic acid. The most common catalyst is chloroplatinic acid and used as a solution in isopropanol. Besides to platinum and palladium, inorganic compounds of nickel, rhodium, ruthenium, copper, and tin depending upon the nature of the unsaturated organic compounds. The organic catalysts other than metallic or inorganic compounds such as triethyl amine, triphenylphosphine, and dimethylformamide may also be used (E. Y. Lukevites and M. G. Voronkov, "Organic Insertion Reactions of Group IV Elements", Consultants Bureau, New York 1966).

In the case of γ-chloropropyltrialkoxysilane preparation, γ-chloropropyltrichlorosilane is prepared by hydrosilating trichlorosilane with allyl chloride, and followed by methanolysis of resulted γ-chloropropyltrialkoxysilane. It is reported that the addition of trichlorosilane to allyl chloride can be carried out at 100° C. for 4–10 hrs in the presence of chloroplatinic acid catalyst under the pressure of 50–300 psi. In this reaction, tetrachlorosilane and propylene are obtained as the by-products due to the exchange reaction of Si—H and C—Cl. The resulted propylene consequently reacts with trichlorosilane to give propyltrichlorosilane (F. P. Mackay, O. W. Steward and P. G. Campbell, J. Am. Chem. Soc., 79, 2764 (1957) and J. L. Speier, J. A. Webster and S. W. Barnes, J. Am. Chem. Soc., 79, 974 (1957)). The γ-chloropropyltrichlorosilane is reacted with alcohols to give hydrogen chloride and the corresponding alkoxy compounds. In this alcoholysis reaction, at least three moles of alcohol are needed per each mole of γ-chloropropyltrichlorosilane. If inert organic solvent are used in the reaction, less hydrogen chloride is dissolved in the products and less hydrolyzed by-products due to the water produced from the reaction of hydrogen chloride and alcohol are produced. In this reaction aliphatic alcohols such as methanol, ethanol, propanol etc. or aromatic alcohol such as phenol may be used.

In general, alkenes having carbon-carbon double bonds are easily react with trichlorosilane. The compounds having the double bond at the end react faster than the compounds having the double bond in the backbone. The linear compounds react faster than the cyclic compounds or aromatic compounds such as styrene. However, for the hydrosilation of acrylonitrile having the strong electron-attracting nitrile group, organic amines or Ni or Fe compounds are better than the noble metal catalysts (W. Noll, "Chemistry and Technology of Silicones", Academic Press, New York, 1968).

In some cases of the preparation of reactive group containing silane coupling agents, trichlorosilane is converted to trialkoxysilane before the hydrosilation with unsaturated compounds to prevent the side reaction between the functional group and the hydrogen chloride produced during the alcoholysis. For example, in the preparation of silane coupling agents containing epoxy or ester groups, trichlorosilane is reacted firstly with alcohol and then hydrosilated with glycidal ether or allylmethacrylate, because epoxy or ester groups are easily reacted with alcohol. Plueddemann and his coworkers disclosed in U.S. Pat. No. 3,258,477 the preparation methods of acrylate substituted silane coupling agent in good yields by hydrosilating vinylacrylate or allylmethacrylate with trialkoxysilane. In this reaction, chloroplatinic acid is reported to be a good catalyst. They also reported that glycidoxypropyl group containing silane coupling agent could be prepared by reacting allylglycidoxy ether with trialkoxysilane (ÄE. P. Plueddemann and G. Fanger, J. Am. Chem. Soc. 81, 2632 (1959)).

We reported that the direct synthesis of Si—H containing bis(silyl)methanes by reacting silicon metal with a mixture of α-chloromethylsilanes and hydrogen chloride or organic chloride which decomposes and eliminates hydrogen chloride at the reaction temperature such as t-butyl chloride. The bis(silyl) methane containing dichlorosilyl group was obtained as the major product and bis(silyl)methane containing trichlorosilyl group was obtained as the minor product (I. N. Jung, S. H. Yeon, and J. S. Han, U.S. Pat. No. 5,233,069 (Aug. 3, 1993)).

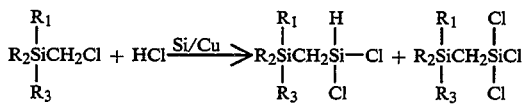

Wherein R₁, R₂ and R₃ may independently be chloride or methyl.

We also found that bis(silyl)methanes having two dichlorosilyl groups at the both ends of the molecule along with bis(silyl)methane having two trichlorosilyl groups at the both ends and bis(silyl)methane having one dichlosilyl group and one trichlorosilyl group at each end were obtained by reacting a mixture of methylene chloride and hydrogen chloride (I. N. Jung, S. H. Yeon, and B. W. Lee, U.S. Pat. No. 5,235,083 (Aug. 10, 1993)).

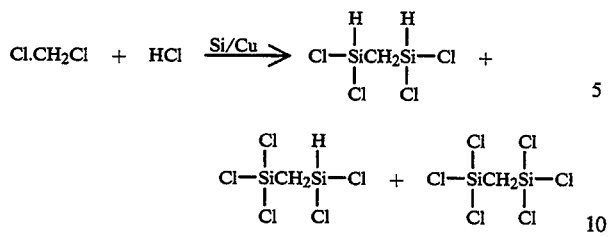

We also reported that two legged silane coupling agents could be prepared by hydrosilating the bis-silylmethanes having Si—H bonds with alkenes, and followed by alcoholysis of the resulting bisalkyl-chlorosilanes (Korean Patent Application No. 92-12998 (Jul. 21, 1992)).

We also reported a process for preparing tris(silyl)methanes by directly reacting a mixture of α,α-dichloromethylsilanes and hydrogen chloride or alkyl chlorides with metallic silicon to give tris(silyl)methanes having two dichlorosilyl groups and the tris(silyl)methanes having one trichlorosilyl group and one dichlorosilyl group in moderately high yields in the presence of copper catalyst at a temperature from 250° C. to 350° C. (Korean Patent Application No. 92-10293 (Jun. 13, 1992)).

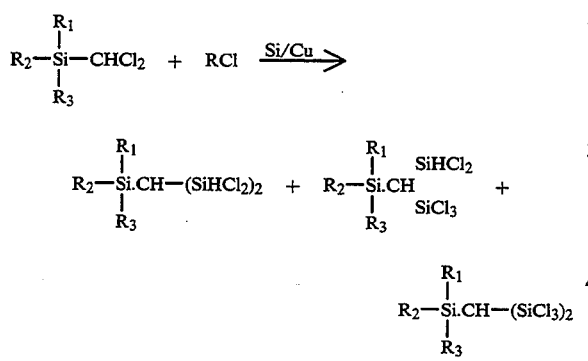

Wherein R represents hydrogen, alkyl(C$_1$-C$_4$) or CH$_2$CH$_2$Cl, and R$_1$, R$_2$, and R$_3$ represent independently hydrogen or chloride.

This invention is relates to the organosilicon compounds represented in Formula (X), (XI), (XII), (XIII), (XIV), (XV), (XVI) and (XVII), and their preparation methods by reacting the trissilylalkanes represented in Formula (I), (II), (III), (IV), (V), (VI), (VII) and (VIII) with cyclohexene or organic compounds having carbon-carbon double bond as represented in Formula (IX) in the presence of catalysts such as chloroplatinic acid, platinum on silica, tributyl amine, compounds of Pd, Rh, Ni, etc.

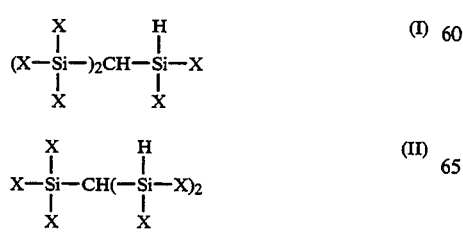 (I)

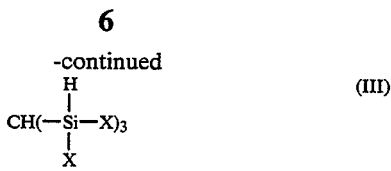 (II)

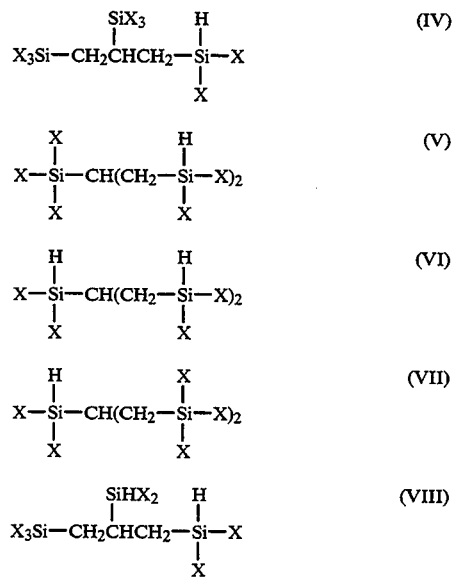

wherein X represents Cl, OR$^1$ (R$^1$ is alkyl(C$_1$-C$_4$)) or OAc in Formula (I), (II), (III), (IV), (V), (VI), (VII) and (VIII).

$$CH_2=CH-R^2 \quad (IX)$$

wherein R$^2$ can be Ph, CH$_2$Cl, C$_n$H$_{2n}$CH$_3$ (n=0-15), Si(Me)$_m$Cl$_{3-m}$ (m=0-3), CF$_3$, CN,

CH=CH$_2$, (CH$_2$)$_4$CH=CH$_2$,

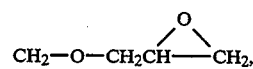

Ph-CH$_2$Cl, CH$_2$CN or cyclohex-3-enyl group.

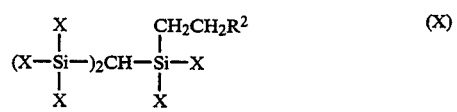 (X)

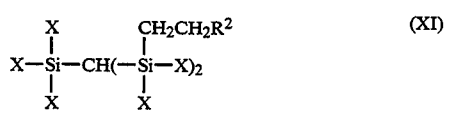 (XI)

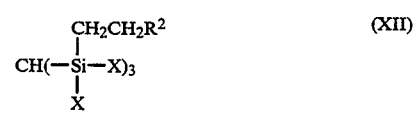 (XII)

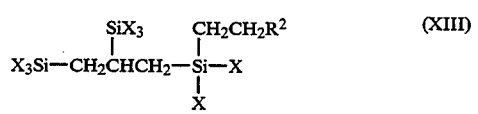 (XIII)

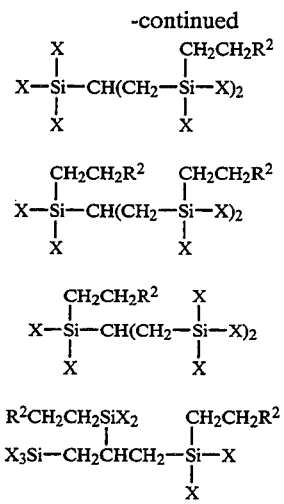

(XIV)
$$X-\underset{\underset{X}{|}}{\overset{\overset{X}{|}}{Si}}-CH(CH_2-\underset{}{Si}-X)_2 \quad | \quad CH_2CH_2R^2$$

(XV)
$$X-\underset{\underset{X}{|}}{\overset{\overset{CH_2CH_2R^2}{|}}{Si}}-CH(CH_2-\underset{}{Si}-X)_2 \quad | \quad CH_2CH_2R^2$$

(XVI)
$$X-\underset{\underset{X}{|}}{\overset{\overset{CH_2CH_2R^2}{|}}{Si}}-CH(CH_2-\underset{}{Si}-X)_2 \quad | \quad X$$

(XVII)
$$X_3Si-CH_2CHCH_2-\underset{\underset{X}{|}}{Si}-X \quad | \quad R^2CH_2CH_2SiX_2 \quad CH_2CH_2R^2$$

wherein X can be Cl, $OR^1$ ($R^1$ Alkyl ($C_1$-$C_4$)) or OAc, and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

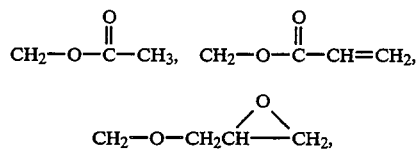

Ph-$CH_2Cl$ or cyclohex-3-enyl group.

We reported that the trissilylalkanes represented in Formula (I), (II), and (III) for the preparation of the three-legged coupling agents could be prepared by reacting directly a mixture of chloroform and hydrogen chloride with metallic silicon (Korean Patent Application No. 12,997 (Jul. 21, 1992)). The compounds represented in Formula (XV), (V), (VX), (VII) and (VIII) were obtained as the by-products from the reaction of mixture of allyl chloride and hydrogen chloride with metallic silicon (Korean Patent Application No. 10292 (Jun. 13, 1992)).

The three legged silane coupling agent producing hydrosilation reactions of the present invention can be run in standard laboratory glasswares or commercial equipments, under inert atmosphere, with units for external heating and cooling, stirring, and for incremental addition of the start silanes or olefins. The reaction can be carried out in most of organic solvents, but it also proceeds in neat condition. When allyl chloride is hydrosilated, the reactor should be pressurized because propylene gas is evolved as a by-product. Otherwise it is not necessary to pressurized the reactor because of the relative high boiling points of trissilylalkanes.

In a typical preparation, trissilylakanes and the hydrosilation catalyst are placed in the reactor under inert atmosphere. The olefin compound is then slowly added to the solution with stirring. In some cases, the reverse addition can be used. The reactions may be sufficiently exothermic at controlled addition rates to maintain to reflux without continuous carting out external heating. After completion of addition, heating may be carried out for a certain period of time to complete the hydrosilation and then the products may be fractionally distilled at atmosphere or under vacuum.

The invention will be further illustrated by the following examples. It is, however, not intended that this invention will be limited by the examples.

EXAMPLE 1

To a 500 ml, two neck, round bottomed flask equipped with a mechanical stirrer and a condenser were added under the dried nitrogen atmosphere, 153 g (0.40 mol) of 2-trichlorosilyl-1,1,1,3,3-pentachloro-1,3-disilapropane, 37.0 g (0.48 mol) of allyl chloride, and 156 μl of 1% chloroplatinic acid catalyst (in isopropylalcohol). The flask was kept in the water bath at 45°-50° C. for 3 hrs with vigorous stirring. After confirming by gas chromatography to complete the reaction, the product was fractionally distilled to give 110 g (0.24 mol, yield 60.0%), which was confirmed by NMR spectrometer (60 MHz) to be 2-trichlorosilyl-1,1,1,3,3,6-hexachloro-1,3-disilahexane. $^1$H NMR($CCl_4$, δ): 2.10 ppm (s, 1H, Si—CH—Si), 1.42 ppm (t, 2H, Si—CH$_2$—C), 2.20 ppm (m, 2H, C—CH$_2$—C), 3.63 ppm (t, 2H, C—CH$_2$—Cl).

The compounds prepared by hydrosilating 2-trichlorosilyl-1,1,1,3,3-pentachloro-1,3-disilapropane with various unsaturated organic compounds according to the procedure described above are listed in Table 1.

TABLE 1

| | | | Products $\left( Cl-\underset{\underset{Cl}{|}}{\overset{\overset{Cl}{|}}{Si}}\right)_2 -CH-\underset{\underset{Cl}{|}}{\overset{\overset{Cl}{|}}{Si}}-A-Y$ | | | |
|---|---|---|---|---|---|---|
| | unsaturated | | | | NMR δ (ppm) | |
| Exp. # | compounds | catalyst | A—Y | Si—CH—Si | A | Y |
| 1 | ⌒⌒Cl | $H_2PtCl_6$ | —(CH$_2$)$_3$Cl | 2.10 (s, 1H) | 1.42 (t, 2H) 2.20 (m, 2H) 3.63 (t, 2H) | — |
| 2 | ⌒⌒CH$_3$ | $H_2PtCl_6$ | —(CH$_2$)$_2$CH$_3$ | 2.03 (s, 1H) | 1.23 (t, 2H) 1.60 (m, 2H) | 1.16 (t, 3H) |
| 3 | ⌒⌒C$_4$H$_9$ | Pt/SiO$_2$ | —(CH$_2$)$_5$CH$_3$ | 2.18 (s, 1H) | 1.50 (m, 10H) | 0.92 (t, 3H) |
| 4 | ⌒⌒CN | Ni | —(CH$_2$)$_3$CN | 2.06 (s, 1H) | 1.62 (t, 2H) 1.92 (t, 2H) | 2.50 (t, 2H) |
| 5 | ⌒⌒Ph | Rh | —(CH$_2$)$_2$Ph | 2.40 (s, 1H) | 1.23 (t, 2H) 2.63 (t, 2H) | 7.12 (s, 5H) |

TABLE 1-continued

Products $$\left(\begin{array}{c}Cl\\|\\Cl-Si-\\|\\Cl\end{array}\right)_2 CH-\begin{array}{c}Cl\\|\\Si-A-Y\\|\\Cl\end{array}$$

| Exp. # | unsaturated compounds | catalyst | A—Y | NMR δ (ppm) Si—CH—Si | A | Y |
|---|---|---|---|---|---|---|
| 6 | cyclohexenyl | Ru | cyclohexyl | 2.30 (s, 1H) | 1.43 (s, 11H) | — |
| 7 | vinyl-Si(CH₃)₂Cl | H₂PtCl₆ | —(CH₂)₂Si(CH₃)₂Cl | 2.10 (s, 1H) | 1.39 (t, 2H) 2.00 (t, 2H) | 0.52 (s, 6H) |
| 8 | $\sim\!\!\!\sim$ | H₂PtCl₆ | —CH₂—CH=CH—CH₃ | 2.00 (s, 1H) | 1.20 (d, 2H) 5.42 (m, 2H) | 1.10 (d, 3H) |
| 9 | $\sim$(CH₂)₄$\sim$ | H₂PtCl₆ | —(CH₂)₆—CH=CH₂ | 2.09 (s, 1H) | 1.33 (m, 12H) | 5.70 (m, 1H) 5.02 (m, 2H) |
| 10 | allyl acetate | H₂PtCl₆ | —(CH₂)₃—O—C(=O)—CH₃ | 2.50 (s, 1H) | 0.95 (t, 2H) 1.62 (m, 2H) 4.00 (t, 2H) | 2.03 (s, 3H) |

EXAMPLE 2

The compounds prepared by hydrosilating 2-dichlorosilyl-1,1,1,3,3-pentachloro-1,3-disilapropane with various unsaturated organic compounds according to the procedure described in Example 1 are listed in Table 2.

TABLE 2

Products $$Cl-\begin{array}{c}Cl\\|\\Si-\\|\\Cl\end{array}CH-\left(\begin{array}{c}Cl\\|\\Si-A-Y\\|\\Cl\end{array}\right)_2$$

| Exp. No. | Unsaturated Compounds | Catalyst | A—Y | NMR δ (ppm) Si—CH—Si | A | Y |
|---|---|---|---|---|---|---|
| 11 | $\sim\!\!\!\sim$Cl | H₂PtCl₆ | —(CH₂)₃Cl | 1.83 (s, 1H) | 1.48 (t, 4H) 2.18 (m, 4H) 3.50 (t, 4H) | — |
| 12 | $\sim$C₄H₉ | Bu₃N/CuCl | —(CH₂)₅CH₃ | 1.88 (s, 1H) | 1.50 (m, 20H) | 0.93 (t, 6H) |
| 13 | $\sim$CF₃ | Pd | —(CH₂)₃CF₃ | 2.03 (s, 1H) | 1.30 (t, 4H) 1.90 (m, 8H) | — |
| 14 | $\sim$CN | Ni | —(CH₂)₂CN | 2.10 (s, 1H) | 1.72 (t, 4H) 2.12 (t, 4H) | — |
| 15 | $\sim\!\!\!\sim$ | H₂PtCl₆ | —CH₂—CH=CH—CH₃ | 1.90 (s, 1H) | 1.23 (d, 4H) 5.80 (m, 4H) | 1.10 (d, 6H) |
| 16 | vinyl-C₆H₄-CH₂Cl | H₂PtCl₆ | —(CH₂)₂—C₆H₄—CH₂Cl | 1.80 (s, 1H) | 1.42 (t, 4H) 2.50 (t, 4H) 7.23 (s, 8H) 4.58 (s, 4H) | — |
| 17 | vinylcyclohexenyl | H₂PtCl₆ | —(CH₂)₂—cyclohexenyl | 1.76 (s, 1H) | 1.20 (t, 4H) 1.43 (m, 4H) | 1.93 (m, 14H) 5.80 (t, 4H) |
| 18 | vinyl-SiCH₃Cl₂ | H₂PtCl₆ | —(CH₂)₂—Si(CH₃)Cl₂ | 1.88 (s, 1H) | 1.42 (t, 4H) 2.03 (t, 4H) | 0.80 (s, 6H) |
| 19 | vinyl-Si(CH₃)₃ | H₂PtCl₆ | —(CH₂)₂—Si(CH₃)₃ | 1.90 (s, 1H) | 1.31 (t, 4H) 1.71 (t, 4H) | 0.32 (s, 18H) |

TABLE 2-continued

Products:

$$Cl-\underset{\underset{Cl}{|}}{\overset{\overset{Cl}{|}}{Si}}-CH\left(\underset{\underset{Cl}{|}}{\overset{\overset{Cl}{|}}{Si}}-A-Y\right)_2$$

| Exp. No. | Unsaturated Compounds | Catalyst | A—Y | NMR δ (ppm) Si—CH—Si | A | Y |
|---|---|---|---|---|---|---|
| 20 | CH₂=CH-CH₂-O-C(=O)-CH₃ | H₂PtCl₆ | —(CH₂)₃—O—C(=O)—CH₃ | 2.09 (s, 1H) | 0.93 (t, 4H) 1.63 (m, 4H) 4.08 (t, 4H) | 2.08 (s, 6H) |

EXAMPLE 3

The compounds prepared by hydrosilating 2-dichlorosilyl-1,1,3,3-tetrachloro-1,3-disilapropane with various unsaturated organic compounds according to the procedure described in Example 1 are listed in Table 3.

EXAMPLE 4

The compounds prepared by hydrosilating 2-trichlorosilyl-1,1,1,3,3-pentachloro-1,4-disilabutane with various unsaturated organic compounds according to the procedure described in Example 1 are listed in Table 4.

TABLE 3

Products:

$$CH\left(\underset{\underset{Cl}{|}}{\overset{\overset{Cl}{|}}{Si}}-A-Y\right)_3$$

| Exp. No. | Unsaturated Compounds | Catalyst | A—Y | NMR δ (ppm) Si—CH—Si | A | Y |
|---|---|---|---|---|---|---|
| 21 | CH₂=CH-CH₂-Cl | Ni | —(CH₂)₃Cl | 1.56 (s, 1H) | 1.50 (t, 6H) 2.30 (m, 6H) 3.50 (t, 6H) | — |
| 22 | CH₂=CH-CH₃ | Ru | —(CH₂)₂CH₃ | 1.50 (s, 1H) | 1.20 (t, 6H) 1.60 (m, 6H) | 1.08 (t, 9H) |
| 23 | CH₂=CH-C₁₀H₂₁ | H₂PtCl₆ | —(CH₂)₁₁CH₃ | 1.40 (s, 1H) | 1.30 (m, 66H) | 0.73 (t, 9H) |
| 24 | CH₂=CH-SiCl₃ | H₂PtCl₆ | —(CH₂)₂SiCl₃ | 1.62 (s, 1H) | 1.45 (t, 6H) 2.13 (t, 9H) | — |
| 25 | CH₂=CH-CH₂-CN | Bu₃N/CuCl | —(CH₂)₃CN | 1.70 (s, 1H) | 1.62 (t, 6H) 2.03 (m, 6H) | 2.50 (t, 6H) |
| 26 | CH₂=CH-(CH₂)₄-CH=CH₂ | H₂PtCl₆ | —(CH₂)₆-CH=CH₂ | 1.53 (s, 1H) | 1.38 (m, 36H) | 5.72 (m, 3H) 5.00 (m, 6H) |
| 27 | CH₂=CH-Ph | H₂PtCl₆ | —(CH₂)₂—Ph | 1.62 (s, 1H) | 1.29 (t, 6H) 2.63 (t, 6H) | 7.20 (s, 15H) |
| 28 | cyclohexene | H₂PtCl₆ | cyclohexyl | 1.43 (s, 1H) | 1.40 (s, 33H) | — |
| 29 | CH₂=CH-CH₂-CF₃ | H₂PtCl₆ | —(CH₂)₃CF₃ | 1.59 (s, 1H) | 1.33 (t, 6H) 2.20 (m, 12H) | — |
| 30 | CH₂=CH-CH₂-O-C(=O)-CH₃ | H₂PtCl₆ | —(CH₂)₃—O—C(=O)—CH₃ | 1.72 (s, 1H) | 0.90 (t, 6H) 1.63 (m, 6H) 4.10 (t, 6H) | 2.30 (s, 9H) |

TABLE 4

| | | | Products $\begin{array}{c} \text{Cl} \quad \text{Cl}_3\text{Si} \quad \text{Cl} \\ | \quad\quad | \quad\quad | \\ \text{Cl}-\text{Si}-\text{CH}_2\text{CH}-\text{Si}-\text{A}-\text{Y} \\ | \quad\quad\quad\quad | \\ \text{Cl} \quad\quad\quad\quad \text{Cl} \end{array}$ | | | NMR δ (ppm) | |
|---|---|---|---|---|---|---|
| Exp. No. | Unsaturated Compounds | Catalyst | A—Y | Si—CH$_2$—CH—Si | A | Y |
| 31 | ⌒Cl | H$_2$PtCl$_6$ | —(CH$_2$)$_3$Cl | 1.90–1.80 (m, 3H) | 1.43 (t, 2H) 2.11 (m, 2H) 3.60 (t, 2H) | — |
| 32 | ⌒CH$_3$ | H$_2$PtCl$_6$ | —(CH$_2$)$_2$CH$_3$ | 1.90–1.80 (m, 3H) | 1.24 (t, 2H) 1.61 (m, 2H) | 1.11 (t, 3H) |
| 33 | ⌒C$_{16}$H$_{33}$ | H$_2$PtCl$_6$ | —(CH$_2$)$_{17}$CH$_3$ | 1.90–1.80 (m, 3H) | 1.25 (m, 34H) | 0.26 (t, 3H) |
| 34 | CH$_3$–Si(Cl)(Cl)–CH=CH$_2$ | H$_2$PtCl$_6$ | —(CH$_2$)$_2$Si(CH$_3$)Cl$_2$ | 1.90–1.80 (m, 3H) | 1.40 (t, 2H) 2.03 (t, 2H) | 0.79 (s, 3H) |
| 35 | ⌒CF$_3$ | H$_2$PtCl$_6$ | —(CH$_2$)$_3$CF$_3$ | 1.90–1.80 (m, 3H) | 1.35 (t, 2H) 2.10 (m, 4H) | — |
| 36 | ⌒CN | Ni | —(CH$_2$)$_3$CN | 1.90–1.80 (m, 3H) | 1.62 (t, 2H) 1.94 (m, 2H) 2.49 (t, 2H) | — |
| 37 | ⌒⌒ | H$_2$PtCl$_6$ | —CH$_2$—CH=CH—CH$_3$ | 1.90–1.80 (m, 3H) | 1.22 (d, 2H) 5.40 (m, 2H) | 1.11 (d, 3H) |
| 38 | CH$_2$Cl-C$_6$H$_4$-CH=CH$_2$ | Pt/SiO$_2$ | —(CH$_2$)$_2$—C$_6$H$_4$—CH$_2$Cl | 1.90–1.80 (m, 3H) | 1.45 (t, 2H) 2.42 (t, 2H) 7.22 (s, 4H) 4.55 (s, 2H) | — |

EXAMPLE 5

The compounds prepared by hydrosilating 3-trichlorosilyl-1,1,5,5-tetrachloro-1,5-disilapentane with various unsaturated organic compounds according to the procedure described in Example 1 are listed in Table 5.

TABLE 5

| | | | Products $\left( \begin{array}{c} \text{Cl} \quad\quad \text{Cl} \\ | \quad\quad | \\ \text{ClSiCH}-\text{CH}_2-\text{Si}-\text{A}-\text{Y} \\ | \quad\quad | \\ \text{Cl} \quad\quad \text{Cl} \end{array} \right)_2$ | | | NMR δ (ppm) | |
|---|---|---|---|---|---|---|
| Exp. No. | Unsaturated Compounds | Catalyst | A—Y | Si—CH(—CH$_2$—Si)$_2$ | A | Y |
| 31 | ⌒Cl | H$_2$PtCl$_6$ | —(CH$_2$)$_3$Cl | 2.14–2.05 (m, 1H) 1.77–1.61 (m, 4H) | 1.41 (t, 4H) 2.09 (m, 4H) 3.59 (t, 4H) | — |
| 32 | ⌒CH$_3$ | Pt/SiO$_2$ | —(CH$_2$)$_2$CH$_3$ | 2.14–2.05 (m, 1H) 1.77–1.61 (m, 4H) | 1.22 (t, 4H) 1.59 (m, 4H) | 1.09 (t, 6H) |
| 33 | ⌒C$_{16}$H$_{33}$ | Rh | —(CH$_2$)$_5$CH$_3$ | 2.14–2.05 (m, 1H) 1.77–1.61 (m, 4H) | 1.29 (m, 20H) | 0.88 (t, 6H) |
| 34 | CH$_3$–Si(Cl)(Cl)–CH=CH$_2$ | Pd | —(CH$_2$)$_2$Si(CH$_3$)$_2$Cl | 2.14–2.05 (m, 1H) 1.77–1.61 (m, 4H) | 1.36 (t, 4H) 1.97 (t, 4H) | 0.50 (s, 12H) |
| 35 | ⌒CF$_3$ | H$_2$PtCl$_6$ | —(CH$_2$)$_2$CF$_3$ | 2.14–2.05 (m, 1H) 1.77–1.61 (m, 4H) | 1.72 (t, 4H) 2.13 (t, 4H) | — |
| 36 | ⌒CN | H$_2$PtCl$_6$ | —(CH$_2$)$_3$CN | 2.14–2.05 (m, 1H) 1.77–1.61 (m, 4H) | 0.94 (t, 4H) 1.60 (m, 4H) 4.00 (t, 4H) | 2.30 (s, 6H) |
| 37 | ⌒⌒ | H$_2$PtCl$_6$ | —(CH$_2$)$_6$⌒ | 2.14–2.05 (m, 1H) 1.77–1.61 (m, 4H) | 1.32 (m, 24H) | 5.70 (m, 2H) 4.98 (m, 4H) |

TABLE 5-continued

Products $$\text{ClSiCH}\begin{matrix}\text{Cl}\\|\\|\\\text{Cl}\end{matrix}\left(\text{CH}_2-\begin{matrix}\text{Cl}\\|\\\text{Si}-\text{A}-\text{Y}\\|\\\text{Cl}\end{matrix}\right)_2$$

| Exp. No. | Unsaturated Compounds | Catalyst | A—Y | NMR δ (ppm) Si—CH(—CH₂—Si)₂ | A | Y |
|---|---|---|---|---|---|---|
| 38 |  | H₂PtCl₆ | —(CH₂)₂ | 2.14–2.05 (m, 1H) 1.77–1.61 (m, 4H) | 1.20 (t, 4H) 1.40 (m, 4H) | 1.90 (m, 14H) 5.78 (t, 4H) |

EXAMPLE 6

The compounds prepared by hydrosilating 3-dichlorosilyl-1,1,5,5-tetrachloro-1,5-disilapentane with various unsaturated organic compounds according to the procedure described in Example 1 are listed in Table 6.

EXAMPLE 7

The compounds prepared by hydrosilating 3-trichlorosilyl-methyl-1,1,1,5,5-pentachloro-1,5-disilapentane with various unsaturated organic compounds according to the procedure described in Example 1 are listed in Table 7.

TABLE 6

Products $$\text{Y}-\text{A}-\text{SiCH}\begin{matrix}\text{Cl}\\|\\|\\\text{Cl}\end{matrix}\left(\text{CH}_2-\begin{matrix}\text{Cl}\\|\\\text{Si}-\text{A}-\text{Y}\\|\\\text{Cl}\end{matrix}\right)_2$$

| Exp. No. | Unsaturated Compounds | Catalyst | A—Y | NMR δ (ppm) Si—CH(—CH₂—Si)₂ | A | Y |
|---|---|---|---|---|---|---|
| 47 |  | H₂PtCl₆ | —(CH₂)₃Cl | 2.00–1.90 (m, 1H) 1.69–1.45 (m, 4H) | 1.44 (t, 6H) 2.12 (m, 6H) 3.60 (t, 6H) | — |
| 48 |  | H₂PtCl₆ | —(CH₂)₂CH₃ | 2.00–1.90 (m, 1H) 1.69–1.45 (m, 4H) | 1.25 (t, 6H) 1.62 (m, 6H) | 1.12 (t, 9H) |
| 49 |  | H₂PtCl₆ | —(CH₂)₁₁CH₃ | 2.00–1.90 (m, 1H) 1.69–1.45 (m, 4H) | 1.32 (m, 66H) | 0.72 (t, 9H) |
| 50 |  | H₂PtCl₆ | —(CH₂)₃CF₃ | 2.00–1.90 (m, 1H) 1.69–1.45 (m, 4H) | 1.35 (t, 6H) 2.10 (m, 12H) | — |
| 51 |  | H₂PtCl₆ | —(CH₂)₃CN | 2.00–1.90 (m, 1H) 1.69–1.45 (m, 4H) | 1.64 (t, 6H) 1.95 (m, 6H) 2.50 (t, 6H) | — |
| 52 |  | H₂PtCl₆ | —CH₂—CH=CH—CH₃ | 2.00–1.90 (m, 1H) 1.69–1.45 (m, 4H) | 1.23 (d, 6H) 5.42 (m, 6H) | 1.10 (d, 9H) |
| 53 |  | H₂PtCl₆ | —(CH₂)₆ | 2.00–1.90 (m, 1H) 1.69–1.45 (m, 4H) | 1.32 (m, 36H) | 5.73 (m, 3H) 5.02 (m, 6H) |
| 54 |  | Pd | —(CH₂)₂—CH₂Cl | 2.00–1.90 (m, 1H) 1.69–1.45 (m, 4H) | 1.46 (t, 6H) 2.43 (t, 6H) 7.21 (s, 12H) 4.55 (s, 6H) | — |

TABLE 7

Products $$\left(\text{Cl}-\begin{matrix}\text{Cl}\\|\\\text{Si}-\text{CH}_2\\|\\\text{Cl}\end{matrix}\right)_2\begin{matrix}\text{Cl}\\|\\\text{CH}-\text{SiA}-\text{Y}\\|\\\text{Cl}\end{matrix}$$

| Exp. No. | Unsaturated Compounds | Catalyst | A—Y | NMR δ (ppm) Si—CH₂—CH—Si | A | Y |
|---|---|---|---|---|---|---|
| 55 |  | H₂PtCl₆ | —(CH₂)₃Cl | 2.00–1.90 (m, 5H) | 1.40 (t, 2H) 2.10 (m, 2H) 3.62 (t, 2H) | — |
| 56 |  | H₂PtCl₆ | —(CH₂)₂CH₃ | 2.00–1.90 (m, 5H) | 1.20 (t, 2H) 1.60 (m, 2H) | 1.10 (t, 3H) |

TABLE 7-continued

Products:

$$\left(\begin{array}{c}Cl\\Cl-Si-CH_2\\Cl\end{array}\right)_2 CH-\overset{Cl}{\underset{Cl}{Si}}A-Y$$

| Exp. No. | Unsaturated Compounds | Catalyst | A—Y | NMR δ (ppm) Si—CH₂—CH—Si | A | Y |
|---|---|---|---|---|---|---|
| 57 | ⌇C₁₆H₃₃ | H₂PtCl₆ | —(CH₂)₁₇CH₃ | 2.00–1.90 (m, 5H) | 1.23 (m, 34H) | 0.25 (t, 3H) |
| 58 | CH₂=CH—Si(CH₃)₃ | H₂PtCl₆ | —(CH₂)₂—Si(CH₃)₃ | 2.00–1.90 (m, 5H) | 1.30 (t, 2H) 1.70 (t, 2H) | 0.30 (s, 9H) |
| 59 | ⌇CN | H₂PtCl₆ | —(CH₂)₂CN | 2.00–1.90 (m, 5H) | 1.72 (t, 2H) 2.10 (t, 2H) | — |
| 60 | ⌇=⌇ | H₂PtCl₆ | —CH₂—CH=CH—CH₃ | 2.00–1.90 (m, 5H) | 1.20 (d, 2H) 5.38 (m, 2H) | 1.10 (d, 3H) |
| 61 | vinyl-cyclohexene | Pt/SiO₂ | —(CH₂)₂—⌬ | 2.00–1.90 (m, 5H) | 1.20 (t, 2H) 1.40 (m, 2H) | 1.89 (m, 7H) 5.78 (t, 2H) |
| 62 | cyclohexene | Ni | cyclohexyl | 2.00–1.90 (m, 5H) | 1.43 (s, 11H) | — |

EXAMPLE 8

The compounds prepared by hydrosilating 3-dichlorosilyl-1,1,1,5,5-pentachloro-1,5-disilapentane with various unsaturated organic compounds according to the procedure described in Example 1 are listed in Table 8.

EXAMPLE 9

To a 1 l, three-neck, round bottomed flask equipped with a mechanical stirrer, a condenser, and a dropping funnel, was placed under the dried nitrogen atmosphere, 70 g (0.15 mol) of 2-trichlorosilyl-1,1,1,3,3,6-hexachloro-1,3-disilahexane prepared in Example 1 in

TABLE 8

Products:

$$\begin{array}{c}Cl_2Si-A-Y\\Cl\quad\quad\quad\quad Cl\\ClSiCH_2CH-CH_2-\overset{|}{Si}-A-Y\\Cl\quad\quad\quad\quad Cl\end{array}$$

| Exp. No. | Unsaturated Compounds | Catalyst | A—Y | NMR δ (ppm) Si—CH(CH₂—Si)₂ | A | Y |
|---|---|---|---|---|---|---|
| 63 | ⌇Cl | H₂PtCl₆ | —(CH₂)₃Cl | 2.02–1.93 (m, 1H) 1.89–1.46 (m, 4H) | 1.49 (t, 4H) 2.15 (m, 4H) 3.64 (t, 4H) | — |
| 64 | ⌇CH₃ | H₂PtCl₆ | —(CH₂)₂CH₃ | 2.02–1.93 (m, 1H) 1.89–1.46 (m, 4H) | 1.26 (t, 4H) 1.62 (m, 4H) | 1.10 (t, 6H) |
| 65 | ⌇C₄H₉ | H₂PtCl₆ | —(CH₂)₅CH₃ | 2.02–1.93 (m, 1H) 1.89–1.46 (m, 4H) | 1.36 (m, 20H) | 0.93 (t, 6H) |
| 66 | CH₂=CH—SiCl₃ | H₂PtCl₆ | —(CH₂)₂SiCl₃ | 2.02–1.93 (m, 1H) 1.89–1.46 (m, 4H) | 1.43 (t, 4H) 2.13 (t, 4H) | — |
| 67 | ⌇CF₃ | H₂PtCl₆ | —(CH₂)₃CF₃ | 2.02–1.93 (m, 1H) 1.89–1.46 (m, 4H) | 1.32 (t, 4H) 2.00 (m, 8H) | — |
| 68 | ⌇CN | H₂PtCl₆ | —(CH₂)₃CN | 2.02–1.93 (m, 1H) 1.89–1.46 (m, 4H) | 1.62 (t, 4H) 1.93 (m, 4H) | — |
| 69 | ⌇=⌇ | H₂PtCl₆ | —CH₂—CH=CH—CH₃ | 2.02–1.93 (m, 1H) 1.89–1.46 (m, 4H) | 1.22 (d, 4H) 5.41 (m, 4H) | 1.11 (d, 6H) |
| 70 | vinyl-cyclohexene | Bu₃N/CuCl | —(CH₂)₂—⌬ | 2.02–1.93 (m, 1H) 1.89–1.46 (m, 4H) | 1.23 (t, 4H) 1.41 (m, 4H) | 1.90 (m, 14H) 5.80 (t, 4H) |

500 ml of diethylether. Through the dropping funnel was added dropwise 48 g (1.5 mol) of methanol with vigorous stirring. After confirming by gas chromatography to complete the reaction, the product was fractionally distilled to give 50 g (yield 80%) which was confirmed by NMR spectrometer (60 MHz) to be 2-trimethoxysilyl-1,1,1,3, -pentamethoxy-6-chloro-1,3-disilahexane. $^1$H NMR (CCl$_4$, δ): -0.10 ppm (s, 1H, Si—CH—Si), 1.42 ppm (s, 6H, Si—OCH$_3$), 3.53 ppm (s, 18H, Si—OCH$_3$).

The trismethoxysilyl compounds prepared by reacting methanol with the trissilyl compounds according to the procedure described in Example 1 through 8 are listed in Table 9.

TABLE 9

| Exp. No. | Reactants Tris(silyl)alkanes | A—Y | Alcohols | Products NMR δ (ppm) Si—CH—Si | OCH₃ | A | Y |
|---|---|---|---|---|---|---|---|
| 71 | (Cl—Si(Cl)(Cl)—CH)₂ structure with Si—A—Y | —(CH₂)₃Cl | CH₃OH | −0.10 (s, 1H) | 3.57 (s, 6H)<br>3.53 (s, 18H) | 1.42 (t, 2H) 2.11 (m, 2H)<br>3.60 (t, 2H) | — |
| 72 | " | —(CH₂)₅CH₃ | | | 3.57 (s, 6H)<br>3.53 (s, 18H) | 1.33 (m, 10H) | 0.93 (t, 3H) |
| 73 | " | —CH₂—CH=CH—CH₃ | | | 3.57 (s, 6H)<br>3.53 (s, 18H) | 1.24 (d, 2H) 5.41 (m, 2H) | 1.30 (d, 3H) |
| 74 | (Cl—Si(Cl)—CH—Si(Cl)—A—Y)₂ | —(CH₂)₃CF₃ | CH₃OH | −0.10 (s, 1H) | 3.57 (s, 12H)<br>3.53 (s, 9H) | 1.38 (t, 4H) 2.09 (m, 8H) | — |
| 75 | " | —(CH₂)₂—C₆H₄—CH₂Cl | | | 3.57 (s, 12H)<br>3.53 (s, 9H) | 1.42 (t, 4H) 2.50 (t, 4H)<br>7.23 (s, 8H) 4.58 (s, 4H) | — |
| 76 | " | —(CH₂)₂Si(CH₃)Cl₂ | | | 3.57 (s, 12H)<br>3.53 (s, 9H) | 1.39 (t, 4H) 2.08 (t, 4H) | 0.53 (s, 12H) |
| 77 | (CH(Si(Cl)(Cl)—A—Y))₃ | —(CH₂)₃CN | CH₃OH | Si—CH—Si or<br>Si—CH₂—CH—Si<br>−0.10 (s, 1H) | 3.57 (s, 18H) | 1.60 (t, 6H) 1.93 (m, 6H) | 2.50 (t, 6H) |
| 78 | " | —(CH₂)₂Ph | | | | 1.21 (t, 6H) 1.42 (m, 6H) | 1.90 (m, 21H)<br>5.80 (t, 6H) |
| 79 | " | —(CH₂)₃OAc | | | | 0.95 (t, 6H) 1.63 (m, 6H)<br>3.80 (t, 6H) | 2.03 (s, 9H) |
| 80 | Cl—Si(Cl)(SiCl₃)—CH₂—CH(Cl)—Si(Cl)(Cl)—A—Y | —(CH₂)₂CH₃ | CH₃OH | −0.10 (m, 3H) | 3.57 (s, 6H)<br>3.53 (s, 18H) | 1.24 (t, 2H) 1.63 (m, 2H) | 0.93 (t, 3H) |

TABLE 9-continued

| Exp. No. | Reactants Tris(silyl)alkanes | A—Y | Alcohols | Products NMR δ (ppm) Si—CH—CH₂—Si | OCH₃ | A | Y |
|---|---|---|---|---|---|---|---|
| 81 | [Cl—Si(Cl)(Cl)—CH₂—CH—Si(Cl)(Cl)—A—Y]₂ structure | —(CH₂)₃CF₃ | | | | 1.30 (t, 2H) 2.00 (m, 4H) | — |
| 82 | same bis structure | —(CH₂)₂CN | CH₃OH | −0.10 (m, 5H) | 3.57 (s, 12H) 3.53 (s, 9H) | 1.72 (t, 4H) 2.13 (t, 4H) | — |
| 83 | Y—A—Si(Cl)(Cl)—CH—(CH₂)₆ structure | —(CH₂)₆— | | | | 1.32 (m, 24H) | 5.80 (m, 2H) 4.90 (m, 4H) |
| 84 | Y—A—Si(Cl)(Cl)—CH—CH₂—Si(Cl)(Cl)—A—Y | —(CH₂)₃Cl | CH₃OH | −0.10 (m, 5H) | 3.57 (s, 18H) | 1.42 (t, 4H) 2.11 (m, 4H) 3.60 (t, 4H) | — |
| 85 | [Cl—Si(Cl)(Cl)—CH₂—CH—Si(A—Y)(Cl)—]₂ | —(CH₂)₂CN | CH₃OH | | | 1.60 (t, 4H) 1.99 (m, 4H) | 2.50 (t, 4H) |
| 86 | same | —(CH₂)₂Si(CH₃)₃ | | | 3.57 (s, 6H) 3.53 (s, 18H) | 1.20 (t, 2H) 2.00 (t, 2H) | 0.50 (s, 9H) |
| 87 | | —(CH₂)₂-cyclohexenyl | | | | 1.21 (t, 2H) 1.42 (m, 2H) | 1.90 (m, 7H) 5.80 (t, 2H) |
| 88 | Cl—Si(Cl₂)—A—Y, Cl—CH₂—CH—Si(Cl)(Cl)—A—Y | —(CH₂)₂CH₃ | CH₃OH | −0.10 (m, 5H) | 3.57 (s, 24H) 3.53 (s, 9H) | 1.30 (t, 4H) 1.70 (m, 4H) | 1.30 (t, 6H) |
| 89 | | —(CH₂)₃CN | | | | 1.50 (t, 4H) 1.99 (m, 4H) | 2.60 (t, 4H) |

EXAMPLE 10

The trisacetoxysilyl compounds prepared by reacting acetic acid anhydride with the trissilyl compounds according to the procedure described in Example 1 through 8 are listed in Table 10.

TABLE 10

| Exp. No. | Reactants Tris(silyl)alkanes | A—Y | Alcohols | Products NMR δ (ppm) Si—CH—Si | OR | A | Y |
|---|---|---|---|---|---|---|---|
| 90 | Cl—Si(Cl)(Cl)—CH[—Si(Cl)(Cl)(Cl)]₂ | —(CH₂)₂CH₃ | C₂H₅OH | −0.10 (s, 1H) | 1.10–1.50 (m, 24H) 3.50–4.10 (m, 16H) | 1.30 (t, 2H) 1.70 (m, 2H) | 1.30 (t, 3H) |
| 91 | {Cl—Si(Cl)—CH—Si(Cl)(Cl)—A—Y}₂ | —(CH₂)₂Ph | C₃H₇OH | −0.10 (s, 1H) | 0.80–1.25 (m, 24H) 1.40–2.10 (m, 16H) 3.60–4.10 (m, 16H) | 1.23 (t, 2H) 2.63 (t, 2H) | 7.10 (s, 5H) |
| 92 | | —(CH₂)₂—cyclohexenyl | C₂H₅OH | −0.10 (s, 1H) | 1.10–1.50 (m, 21H) 3.50–4.10 (m, 14H) | 1.21 (t, 4H) 1.43 (m, 4H) | 2.03 (m, 14H) 6.00 (t, 4H) |
| 93 | {Cl—Si(Cl)(Cl)—A—Y}₃CH | —(CH₂)₂—Si(CH₃)₃ | C₄H₉OH | −0.10 (s, 1H) | 0.70–1.20 (m, 21H) 1.20–1.90 (m, 28H) 3.40–4.00 (m, 14H) | 1.33 (t, 4H) 1.73 (t, 4H) | 0.33 (s, 18H) |
| 94 | | —(CH₂)₁₁CH₃ | C₃H₇OH | −0.10 (s, 1H) | 0.80–1.25 (m, 18H) 1.40–2.10 (m, 12H) 3.60–4.10 (m, 12H) | 1.30 (m, 66H) | 0.80 (t, 9H) |
| 95 | Cl₃Si—CH₂—CH(SiCl₃)—Si(Cl)(Cl)—A—Y | —(CH₂)₃CN | Ac₂O | −0.10 (s, 1H) | 1.98 (s, 18H) | 1.60 (t, 6H) 1.92 (m, 6H) | 2.60 (t, 6H) |
| 96 | | —(CH₂)₃CF₃ | C₂H₅OH | −0.10 (m, 3H) | 1.10–1.50 (m, 24H) 3.50–4.10 (m, 16H) | 1.30 (t, 2H) 2.00 (m, 4H) | — |
| 97 | | —CH₂—CH=CH—CH₃ | C₄H₉OH | −0.10 (m, 3H) | 0.70–1.20 (m, 24H) 1.20–1.90 (m, 32H) 3.40–4.00 (m, 16H) | 1.23 (d, 2H) 5.92 (m, 2H) | 1.50 (d, 3H) |
| 98 | {Cl—Si(Cl)—CH₂—Si(Cl)(Cl)—A—Y}₂ | —(CH₂)₅CH₃ | Ac₂O | −0.10 (s, 5H) | 2.30 (s, 21H) | 1.80 (m, 20H) | 0.98 (t, 6H) |
| 99 | | —(CH₂)₂CN | C₃H₇OH | −0.10 (m, 5H) | 0.80–1.25 (m, 21H) | 1.72 (t, 4H) 2.23 (t, 4H) | — |

TABLE 10-continued

| Exp. No. | Reactants | | | Products NMR δ (ppm) | | | |
|---|---|---|---|---|---|---|---|
| | Tris(silyl)alkanes | A—Y | Alcohols | Si—CH—Si | OR | A | Y |
| 100 | Y—A—SiCH(Cl)(CH₂—Si(Cl)(Cl)—A—Y)₂ with Cl substituents | —(CH₂)₃Cl | C₂H₅OH | −0.10 (m, 5H) | 1.40–2.10 (m, 14H) 3.60–4.10 (m, 14H) | 1.48 (t, 6H) 2.20 (m, 6H) 3.58 (t, 6H) | — |
| 101 | (Cl—Si(Cl)(Cl)—CH₂—CH(—A—Y)—)₂ | —(CH₂)₆— | C₄H₉OH | −0.10 (m, 5H) | 0.70–1.20 (m, 18H) 1.20–1.90 (m, 24H) 3.40–4.00 (m, 12H) | 1.38 (m, 36H) | 5.77 (m, 3H) 5.00 (m, 6H) |
| 102 | (Cl—Si(Cl)(Cl)—CH₂—CH(—A—Y)—)₂ | —(CH₂)₂CH₃ | C₂H₅OH | −0.10 (m, 5H) | 1.10–1.50 (m, 24H) 3.50–4.10 (m, 16H) | 1.29 (t, 2H) 1.80 (m, 2H) | 1.18 (t, 3H) |
| 103 | Cl₂Si(A—Y)—CH₂—CH(Cl)—CH₂—Si(Cl)(Cl)—A—Y | —(CH₂)₂CN | C₃H₇OH | −0.10 (m, 5H) | 0.80–1.25 (m, 24H) 1.40–2.10 (m, 16H) 3.60–4.10 (m, 16H) | 1.68 (t, 2H) 2.03 (t, 2H) | 2.80 (t, 2H) |
| 104 | Cl₂Si(A—Y)—CH₂—CH(Cl)—CH₂—Si(Cl)(Cl)—A—Y | —(CH₂)₃CF₃ | C₂H₅OH | −0.10 (m, 5H) | 1.10–1.50 (m, 21H) 3.50–4.10 (m, 14H) | 1.30 (t, 4H) 1.90 (m, 8H) | — |
| 105 | | —(CH₂)₂-cyclohexenyl | C₃H₇OH | −0.10 (m, 5H) | 0.85–1.25 (m, 21H) 1.40–2.10 (m, 14H) 3.60–4.10 (m, 14H) | 1.20 (t, 4H) 1.43 (m, 4H) | 1.99 (m, 14H) 5.80 (t, 4H) |

What is claimed is:

1. A trissilylalkane represented by formula (X);

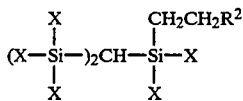

wherein X can be Cl, $OR^1(R^1=C_1-C_4$ alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

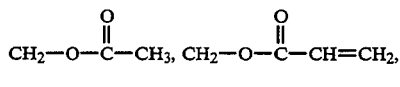

Ph-$CH_2Cl$ or cyclohex-3-enyl group.

2. A trissilylalkane represented by formula (XI);

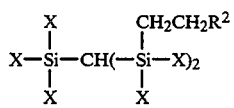

wherein X can be Cl, $OR^1(R^1=C_1-C_4$ alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

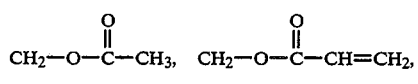

Ph-$CH_2Cl$ or cyclohex-3-enyl group.

3. A trissilylalkane represented by formula (XII);

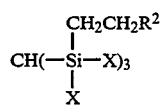

wherein X can be Cl, $OR^1(R^1=C_1-C_4$ alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

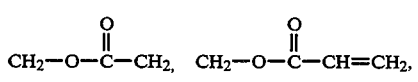

Ph-$CH_2Cl$ or cyclohex-3-enyl group.

4. A trissilyalkane represented by formula (XIII);

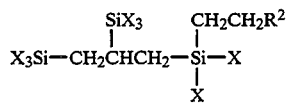

wherein X can be Cl, $OR^1(R^1=C_1-C_4$ alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

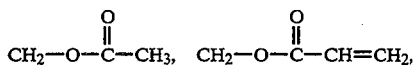

Ph-$CH_2Cl$ or cyclohex-3-enyl group.

5. A trissilylalkane represented by formula (XIV);

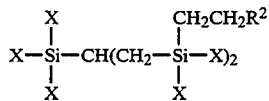

wherein X can be Cl, $OR^1(R^1=C_1-C_4$alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $CH_2)_4CH=CH_2$,

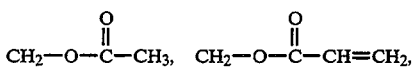

Ph-$CH_2Cl$ or cyclohex-3-enyl group.

6. A trissilylalkane represented by formula (XV);

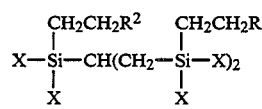

wherein X can be Cl, $OR^1(R^1=C_1-C_4$alkyl) or OAc and $R^2$ can be Ph, $CH_2Cl$, $C_nH_{2n}CH_3$ (n=0-15), $Si(Me)_mCl_{3-m}$ (m=0-3), $CF_3$, CN, $CH_2CN$, $CH=CH_2$, $(CH_2)_4CH=CH_2$,

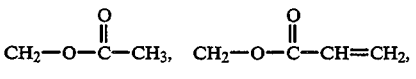

Ph-$CH_2Cl$ or cyclohex-3-enyl group.

7. A trissilylalkane represented by formula (XVI);

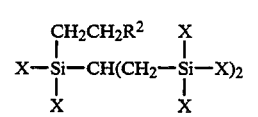

wherein X can be Cl, $OR^1$ ($R^1=C_1$-$C_4$ alkyl) or OAc and $R^2$ can be Ph, $CH_2Cl$, $C_nH_{2n}CH_3$ (n=0-15), Si(-Me)$_m$Cl$_{3-m}$ (m=0-3), $CF_3$, CN, $CH_2CN$, $CH=CH_2$, $(CH_2)_4CH=CH_2$,

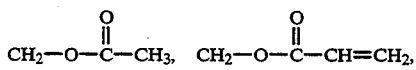

Ph-CH$_2$Cl or cyclohex-3-enyl group.

8. A trissilylalkane represented by formula (XVII);

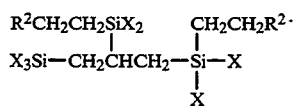

wherein X can be Cl, $OR^1$ ($R^1=C_1$-$C_4$ alkyl) or OAc and $R^2$ can be Ph, $CH_2Cl$, $C_nH_{2n}CH_3$ (n=0-15), Si(-Me)$_m$Cl$_{3-m}$ (m=0-3), $CF_3$, CN, $CH_2CN$, $CH=CH_2$, $CH_2)_4CH=CH_2$,

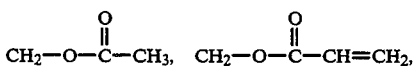

Ph-CH$_2$Cl or cyclohex-3-enyl group.

9. A method for preparation of the compounds according to the formula (X) in claim 1 which comprises hydrosilating trissilylalkanes represented by formula (I) with cyclohexene or organic compounds represented by formula (IX) in the presence of hydrosilating catalyst;

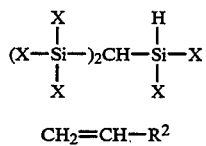

wherein X can be Cl, $OR^1$ ($R^1=C_1$-$C_4$ alkyl) or OAc, and $R^2$ can be Ph, $CH_2Cl$, $C_nH_{2n}CH_3$ (n=0-15), Si(-Me)$_m$Cl$_{3-m}$ (m=0-3), $CF_3$, CN,

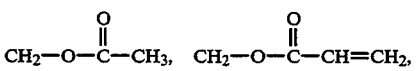

CH=CH$_2$, (CH$_2$)$_4$CH=CH$_2$,

Ph-CH$_2$Cl, CH$_2$CN or cyclohex-3-enyl group.

10. A method for preparation of the compounds according to the formula (XI) in claim 2 which comprises hydrosilating trissilylalkanes represented by formula (II) with cyclohexene or organic compounds represented by formula (IX) in the presence of hydrosilating catalyst;

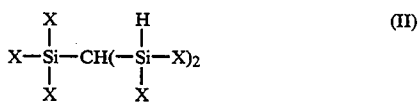

wherein X can be Cl, $OR^1$ ($R^1=C_1$-$C_4$ alkyl) or OAc, and $R^2$ can be Ph, $CH_2Cl$, $C_nH_{2n}CH_3$ (n=0-15), Si(-Me)$_m$Cl$_{3-m}$ (m=0-3), $CF_3$, CN,

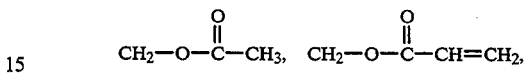

CH=CH$_2$, (CH$_2$)$_4$CH=CH$_2$,

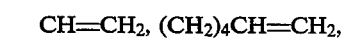

Ph-CH$_2$Cl, CH$_2$CN or cyclohex-3-enyl group.

11. A method For preparation of the compounds according to the formula (XII) in claim 3 which comprises hydrosilating trissilylalkanes represented by formula (III) with cyclohexene or organic compounds represented by formula (IX) in the presence of hydrosilating catalyst;

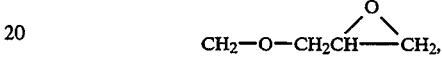

wherein X can be Cl, $OR^1$ ($R^1=C_1$-$C_4$ alkyl) or OAc, and $R^2$ can be Ph, $CH_2Cl$, $C_nH_{2n}CH_3$ (n=0-15), Si(-Me)$_m$Cl$_{3-m}$ (m=0-3), $CF_3$, CN,

CH=CH$_2$, (CH$_2$)$_4$CH=CH$_2$,

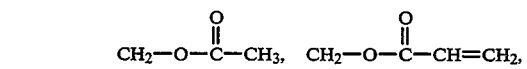

Ph-CH$_2$Cl, CH$_2$CN or cyclohex-3-enyl group.

12. A method For preparation of the compounds according to the formula (XIII) in claim 4 which comprises hydrosilating trissilylalkanes represented by formula (IV) with cyclohexene or organic compounds represented by formula (IX ) in the presence of hydrosilating catalyst;

wherein X can be Cl, $OR^1$ ($R^1=C_1$-$C_4$ alkyl) or OAc, and $R^2$ can be Ph, $CH_2Cl$, $C_nH_{2n}CH_3$ (n=0-15), Si(-Me)$_m$Cl$_{3-m}$ (m=0-3), $CF_3$, CN,

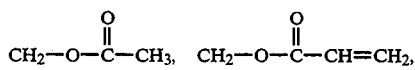

CH=CH$_2$, (CH$_2$)$_4$CH=CH$_2$,

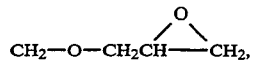

Ph-CH$_2$Cl, CH$_2$CN or cyclohex-3-enyl group.

13. A method for preparation of the compounds according to the formula (XIV) in claim 5 which comprises hydrosilating trissilylalkanes represented by formula (V) with cyclohexene or organic compounds represented by formula (IX) in the presence of hydrosilating catalyst;

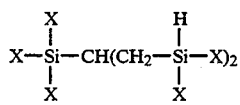
(V)

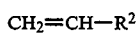
(IX)

wherein X can be Cl, OR$^1$(R$^1$=C$_1$-C$_4$ alkyl ) or OAc, and R$^2$ can be Ph, CH$_2$Cl, C$_n$H$_{2n}$CH$_3$ (n=0-15), Si(-Me)$_m$Cl$_{3-m}$ (m=0-3), CF$_3$CN,

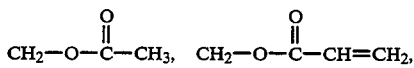

CH=CH$_2$, (CH$_2$)$_4$CH=CH$_2$,

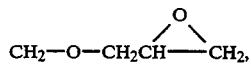

Ph-CH$_2$Cl, CH$_2$CN or cyclohex-3-enyl group.

14. A method for preparation of the compounds according to the formula (XV) in claim 6 which comprises hydrosilating trissilylalkanes represented by formula (VI) with cyclohexene or organic compounds represented by formula (IX) in the presence of hydrosilating catalyst;

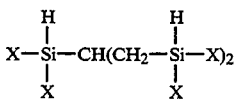
(VI)

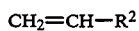
(IX)

wherein X can be Cl, OR$^1$(R$^1$=C$_1$-C$_4$ alkyl) or OAc, and R$^2$ can be Ph, CH$_2$Cl, C$_n$H$_{2n}$CH$_3$ (n=0-15), Si(-Me)$_m$Cl$_{3-m}$ (m=0-3)

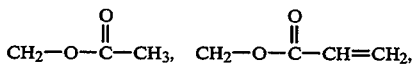

CH=CH$_2$, (CH$_2$)$_4$CH=CH$_2$,

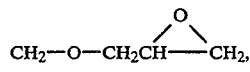

Ph-CH$_2$Cl, CH$_2$CN or cyclohex-3-enyl group.

15. A method for preparation of the compounds according to the formula (XVI) in claim 7 which comprises hydrosilating trissilylalkanes represented by formula (VII) with cyclohexene or organic compounds represented by in formula (IX) the presence of hydrosilating catalyst;

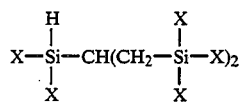
(VII)

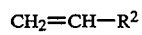
(IX)

where in X can be Cl, OR$^1$(R$^1$=C$_1$-C$_4$ alkyl ) or OAc, and R$^2$ can be Ph, CH$_2$Cl, C$_n$H$_{2n}$CH$_3$ (n=0-15), Si(-Me)$_m$Cl$_{3-m}$ (m=0-3) CF$_3$, CN,

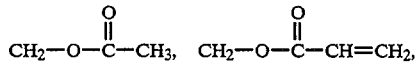

CH=CH$_2$, (CH$_2$)$_4$CH=CH$_2$,

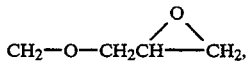

Ph-CH$_2$Cl, CH$_2$CN or cyclohex-3-enyl group.

16. A method for preparation of the compounds according to the formula (XVII) in claim 8 which comprises hydrosilating trissilylalkanes represented by formula (VIII) with cyclohexene or organic compounds represented by formula (IX) in the presence of hydrosilating catalyst;

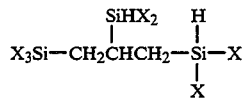
(VIII)

(IX)

wherein X can be Cl, OR$^1$(R$^1$=C$_1$-C$_4$ alkyl) or OAc, and R$^2$ can be Ph, CH$_2$Cl, Cl$_n$H$_{2n}$CH$_3$ (n=0-15), Si(-Me)$_m$C$_{3-m}$ (m=0-3), CF$_3$, CN,

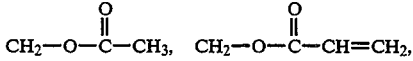

CH=CH$_2$, (CH$_2$)$_4$CH=CH$_2$,

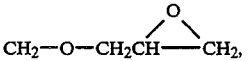

Ph-CH$_2$Cl, CH$_2$CN or cyclohex-3-enyl group.

17. The method according to claim 9, wherein the hydrosilation catalyst Comprises at least one compound selected from the group of chloroplatinic acid, platinum on silica, tributyl amine and inorganic compounds of Pd, Rh, or Ni.

* * * * *